(12) United States Patent
Koltzenburg et al.

(10) Patent No.: US 8,541,012 B2
(45) Date of Patent: Sep. 24, 2013

(54) AQUEOUS DISPERSION COMPRISING PESTICIDE PARTICLES AND DISSOLVED SACCHARIDE

(75) Inventors: Sebastian Koltzenburg, Dannstadt-Schauernheim (DE); Andreas Bauder, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/140,039

(22) PCT Filed: Dec. 10, 2009

(86) PCT No.: PCT/EP2009/066835
§ 371 (c)(1),
(2), (4) Date: Jun. 16, 2011

(87) PCT Pub. No.: WO2010/079036
PCT Pub. Date: Jul. 15, 2010

(65) Prior Publication Data
US 2011/0257010 A1 Oct. 20, 2011

(30) Foreign Application Priority Data
Dec. 18, 2008 (EP) .................................... 08172198

(51) Int. Cl.
*A01N 25/00* (2006.01)

(52) U.S. Cl.
USPC ........................ 424/405; 504/116.1

(58) Field of Classification Search
USPC ........................ 424/405; 504/116.1
See application file for complete search history.

(56) References Cited

U.S. PATENT DOCUMENTS

| 3,535,423 | A | 10/1970 | Ordas |
| 4,405,605 | A | 9/1983 | Itzel |
| 5,001,150 | A | 3/1991 | Yap |
| 6,426,082 | B1 * | 7/2002 | Ueda et al. .................... 424/408 |
| 2002/0115565 | A1 * | 8/2002 | Asrar et al. .................... 504/100 |
| 2007/0122436 | A1 | 5/2007 | Koltzenburg et al. |

FOREIGN PATENT DOCUMENTS

| CN | A 1411718 | 4/2003 |
| CN | A 1535575 | 10/2004 |
| EP | 0031454 A2 | 7/1981 |
| WO | WO 96/36226 A | 11/1996 |
| WO | WO 97/13503 A | 4/1997 |
| WO | WO 2004/047516 A | 6/2004 |
| WO | WO 2005/046328 | 5/2005 |

OTHER PUBLICATIONS

International Preliminary Report on Patentability, PCT/EP2009/066835, Jun. 21, 2011.
Müller et al. (Editor), Emulsions and Nanosuspensions for the Formulation of Poorly Soluble Drugs, Medpharm Scientific Publishers Stuttgart, 1998.
Kokini, Jozef L. and Fischbach, E. Raymond, "*Storage Stability of Model Sucrose or Salt Added O/W Emulsions Through Steady Shear and Creep Rheological Measurements*", Journal of Food Processing and Preservation, 1989, vol. 12, pp. 293-308, Food & Nutrition Press, Inc., Trumbull, CT.
International Search Report PCT/EP2009/066835.

\* cited by examiner

*Primary Examiner* — Fereydoun G Sajjadi
*Assistant Examiner* — Danielle Sullivan
(74) *Attorney, Agent, or Firm* — Brinks Hofer Gilson & Lione

(57) ABSTRACT

The present invention relates to an aqueous dispersion comprising solid pesticide particles with a particle size of below 10 μm and a saccharide which is dissolved in the aqueous phase. The invention furthermore relates to a process for the preparation of a dispersion according to the invention by bringing a pesticide and a saccharide, which is a monosaccharide, a disaccharide or a mixture of mono- and disaccharide, into contact and dispersing them. A further subject matter relates to the use of a saccharide for slowing down the particle growth of pesticide particles with a particle size of up to 10 μm in aqueous dispersion, to the use of the dispersion or the solid composition for controlling phytopathogenic fungi and/or undesired vegetation and/or undesired attack by insects or mites and/or for regulating the growth of plants. Finally, the present invention also relates to seed, dressed with the dispersion or the solid composition.

19 Claims, No Drawings

AQUEOUS DISPERSION COMPRISING PESTICIDE PARTICLES AND DISSOLVED SACCHARIDE

This application is a National Stage application of International Application No. PCT/EP2009/066835, filed Dec. 10, 2009, the entire contents of which are hereby incorporated herein by reference. This application also claims priority under 35 U.S.C. §119 to European Patent Application No. 08172198.7, filed Dec. 18, 2008, the entire contents of which are hereby incorporated herein by reference.

The present invention relates to an aqueous dispersion comprising solid pesticide particles with a particle size of below 10 μm and a saccharide which is dissolved in the aqueous phase. The invention furthermore relates to a process for the preparation of a dispersion according to the invention by bringing a pesticide and a saccharide, which is a monosaccharide, a disaccharide or a mixture of mono- and disaccharide, into contact. A further subject matter relates to the use of a saccharide for slowing down the particle growth of pesticide particles with a particle size of up to 10 μm in aqueous dispersion, to the use of the dispersion or of the solid composition for controlling phytopathogenic fungi and/or undesired vegetation and/or undesired attack by insects or mites and/or for regulating the growth of plants, by allowing the dispersion or the solid composition to act on the respective pests, their environment and/or the plants to be protected from the respective pest, on the soil and/or on undesired plants and/or on the useful plants and/or their environment, and to the use of the dispersion or of the solid composition for controlling undesired attack by insects or mites on plants and/or for controlling phytopathogenic fungi and/or for controlling undesired vegetation by treating seed of useful plants with the dispersion or the solid composition. Finally, the present invention also relates to seed, treated with the dispersion or the solid composition. Combinations of preferred features with other preferred features are comprised by the present invention.

Many pesticides are ideally provided in the form of aqueous systems. Naturally, this makes efficient application of active substances which are insoluble in water more difficult, since the concentration available in the aqueous solution, and hence the biological activity are low. It is known that the solubility, dispersibility and bioavailability of active substance particles can be increased by enlarging the particle surface area, that is to say by making the particle size smaller while retaining the same total amount. For example, the penetration of biological membranes is made easier when particle size is smaller. Likewise, dissolution rate and apparent solubility of the particles are increased; see also Müller R H, Benita S, Böhm B H L, eds. Stuttgart, Germany: Medpharm Scientific Publishers; 1998. This means at the same time that the active substance quantities required when using particles on the magnitude of a few micrometers, preferably less than one micrometer, are smaller for achieving the same effect than when the active substance is used in the form of larger particles.

Surface-active substances which inhibit the agglomeration of the particles are frequently employed for the colloidal stabilization of systems with particle sizes of below ten micrometers. Typical stabilizers are low-molecular-weight surfactants or oligomers. Higher-molecular-weight adjuvants, such as, for example, colloids and amphiphilic polymers, however, also offer the possibility of stabilizing active substance particles in small dimensions. Likewise, it is possible to osmotically stabilize ultra finely divided dispersions against Ostwald ripening by adding substances which are extremely sparingly soluble in water, such as, for example, hexadecane.

U.S. Pat. No. 6,426,028 B1 discloses an aqueous suspension of a microencapsulated pesticide, it being possible for the suspension to comprise from 3 to 30% by weight of a monosaccharide.

WO 2004/047516 discloses an aqueous compositon for the treatment of seed, which composition may comprise fertilizer, binder and from 0 to 25% by weight of sugar. It is possible to add a pesticide in addition to the water-soluble fertilizer.

EP 0 031 454 discloses a liquid fungicide formulation in which dimethylformamide and/or N-methylpyrrolidone are employed as solvent, and stabilizing additions of from 1 to 40% by weight of saccharides.

Aqueous dispersions comprising pesticide particles with a particle size of less than 10 μm and a saccharide dissolved in the aqueous phase are generally known:

WO 2005/046328 discloses active substance formulations comprising at least one active substance and at least one random copolymer prepared by free-radical polymerization and composed of selected monomers. The particle diameter of the pesticide amounts to less than 1 μm. The formulation may comprise glucose or sucrose as plasticizer.

WO 1997/13503 discloses a method for syntheseizing nanoparticles which comprises combining an agent, e.g. a pesticide, with a matrix material, e.g. sucrose, and spray drying the mixture from solution.

The disadvantage of the prior art is, inter alia, that polymers must be added whose synthesis is complicated, and/or that the particle formation process takes place during the drying process and can therefore be controlled only with difficulty.

It was an object of the present invention to find novel ways of stably formulating pesticide particles with a particle size of below 10 μm. In particular, it was intended that the method should manage with inexpensive, readily available compositions which are also very environmentally friendly.

The object was achieved by an aqueous dispersion comprising solid pesticide particles with a particle size of below 10 μm and a saccharide which is dissolved in the aqueous phase, wherein the saccharide is a monosaccharide, a disaccharide or a mixture of mono- and disaccharide, and the total content of mono- and disaccharide amounts to at least 15% by weight based on the aqueous dispersion wherein the pesticide is insoluble in water and wherein the pesticide particles are amorphous.

An aqueous dispersion usually comprises water as the continuous phase and solid or liquid particles as the disperse phase. The dispersion is preferably a suspension whose disperse phase comprises solid particles. The dispersion usually comprises at least 5% by weight, preferably at least 15% by weight, especially preferably at least 20% by weight, of water. In most cases, the dispersion comprises from 1 to 85% by weight, preferably from 5 to 80% by weight, especially preferably from 10 to 60% by weight, of water.

The dispersion according to the invention usually has a viscosity of at least 100 mPas, preferably at least 200, especially preferably at least 300 mPas, and specifically at least 500 mPas at 20° C. In most cases, the viscosity amounts to no more than 10 000 mPas, preferably no more than 5000 mPas and in particular no more than 2000 mPas at 20° C. The viscosity can be determined by the Brookfield method.

In most cases, the pesticide particles comprise at least 80% by weight, preferably at least 90% by weight, especially preferably at least 95% by weight and in particular at least 99% by weight of solid pesticide. The pesticide particles preferably consist of pesticide. In most cases, the pesticide particles are free from a polymeric coating composition. Polymeric coating compositions comprise, for example, polymers such as polyurethane, polyamide, polyacrylate, melamin, gelatin, albumin, chitosan, urea/formaldehyde resins, melamin/formaldehyde resins. These polymers coat, or encapsulate, the pesticide with a polymeric layer.

The particle size of the pesticide particles usually refers to the number-average particle size. It is below 10 µm, preferably below 2 µm, especially preferably below 1 µm. In most cases, the particle size is above 5 nm, preferably above 20 nm, especially preferably above 50 nm. In most cases, the particle size is determined by means of photon correlation spectroscopy (dynamic light scattering), for example using an apparatus of the Brookhaven Instruments BI90 brand. In this measuring method, the sample preparation, for example the dilution to the measuring concentration, depends, inter alia, on the fineness and concentration of the active substances in the dispersion sample and on the instrument used. The procedure must be established for the system in question and is known to the skilled worker.

The solid pesticide particles may be amorphous. Amorphous means that the molecular units of a homogeneous solid are not arranged in the form of crystal lattices. Amorphous active substance particles means that the particles are largely free from crystalline active substance, with preferably from 80 to 100% by weight, in particular from 90 to 100% by weight, of the material being in amorphous form. Amorphous forms can be distinguished from crystalline forms by a variety of methods, for example by examination under a microscope in polarized light, differential scanning calorimetry (DSC), x-ray diffraction or solubility comparisons, preferably by means of DSC.

The saccharide is a monosaccharide, a disaccharide or a mixture of mono- and disaccharide. This means that at least one monosaccharide, at least one disaccharide or a mixture of at least one mono- and at least one disaccharide may be present. The saccharide is preferably a disaccharide, in particular sucrose.

Examples of suitable monosaccharides are pentoses and pentuloses, and the hexoses and hexuloses. Suitable pentoses are, for example, D-ribose, D-xylose and L-arabinose. Examples of suitable hexoses are D-glucose, D-mannose and D-galactose. Suitable hexuloses are, for example, D-fructose and sorbose. Further suitable monosaccharides are, for example, the 6-desoxy sugars, such as L-fucose and L-rhamnose. Mixtures of the above monosaccharides are also suitable. Preferred monosaccharides are D-glucose and D-fructose.

Examples of suitable disaccharides are sucrose, maltose, lactose, trehalose, cellobiose, gentiobiose, isomaltose, lactulose, maltulose, melibiose, neohesperidose, neotrehalose, nigerose, palatinose, rutinose, sophorose, or mixtures of the above disaccharides. Preferred disaccharides are sucrose, maltose and lactose, in particular sucrose.

Examples of suitable mixtures of mono- and disaccharides are mixtures of above-mentioned monosaccharides and disaccharides.

The total content of mono- and disaccharide in the aqueous dispersion amounts to at least 15% by weight, preferably to at least 20% by weight, especially preferably to at least 25% by weight, based on the aqueous dispersion. The total content usually amounts to no more than 90% by weight, preferably no more than 70% by weight, especially preferably no more than 60% by weight, based on the aqueous dispersion.

The term pesticide refers to at least one active substance selected from the group of the fungicides, insecticides, nematicides, herbicides, safeners and/or growth regulators. Preferred pesticides are fungicides, insecticides and herbicides. Mixtures of pesticides from two or more of the abovementioned classes may also be used. The skilled worker is familiar with those pesticides, which can be found for example in Pesticide Manual, 14th Ed. (2006), The British Crop Protection Council, London.

Suitable insecticides are insecticides from the class of the carbamates, organophosphates, organochlorine insecticides, phenylpyrazoles, pyrethroids, neonicotinoids, spinosins, avermectins, milbemycins, juvenile hormone analogs, alkyl halides, organotin compounds, nereistoxin analogs, benzoylureas, diacylhydrazines, METI acaricides, and insecticides such as chloropicrin, pymetrozin, flonicamid, clofentezin, hexythiazox, etoxazole, diafenthiuron, propargite, tetradifon, chlorfenapyr, DNOC, buprofezin, cyromazin, amitraz, hydramethylnon, acequinocyl, fluacrypyrim, rotenone, or their derivatives.

Suitable fungicides are fungicides from the classes dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzylcarbamates, carbamates, carboxamides, carboxylic acid amides, chloronitriles, cyanoacetamideoximes, cyanoimidazoles, cyclopropanecarboxamides, dicarboximides, dihydrodioxazines, dinitrophenylcrotonates, dithiocarbamates, dithiolanes, ethylphosphonates, ethylaminothiazolecarboxamides, guanidines, hydroxy-(2-amino) pyrimidines, hydroxyanilides, imidazoles, imidazolinones, inorganic substances, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiocarbamates, thiophanates, thiophenecarboxamides, toluamides, triphenyltin compounds, triazines, triazoles.

Suitable herbicides are herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ethers, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidiniumdiones, pyrimidinyl (thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

Preferred pesticides are those which are insoluble in water. Suitable insoluble pesticides are those which are soluble at 20° C. in water to no more than 3% by weight, preferably no more than 1% by weight, preferably no more than 0.1% by weight and very especially preferably no more than 0.01%. Examples of suitable insoluble pesticides are (solubility in water at 20° C. in each case in parentheses) pyraclostrobin (1.9 mg/l), epoxiconazole (6.6 mg/l), prochloraz (34 mg/l), preferably pyraclostrobin.

The pesticides employed are frequently solids at 20° C. The melting point of the active substances is preferably at least 30° C. and preferably at least 40° C.

The invention also relates to a method of preparing the dispersion according to the invention by bringing a pesticide and a saccharide which is a monosaccharide, a disaccharide or a mixture of mono- and disaccharide, into contact. It is possible to bring the dispersed pesticide into contact with the saccharide, or to disperse the mixture after active substances and saccharide have been brought into contact. The skilled worker is generally familiar with a wide range of methods for dispersing active substances such as pesticides. Examples of suitable processes are precipitation methods, emulsification methods, evaporation methods, melt emulsification or milling methods, preferably precipitation methods. It is preferred to bring the pesticide and the saccharide into contact in an aqueous system and to disperse the mixture. It is especially preferred to employ the saccharide in aqueous solution. Suitable pesticides are the pesticides described above. The pesticide is preferably insoluble in water. Suitable saccharides are the above-described saccharides. The preferred saccharide is sucrose.

Especially preferred methods are carried out in such a way that the saccharide is dissolved in water, the pesticide is dissolved in a water-miscible organic solvent, and the solutions of the saccharide and of the pesticide are mixed turbulently (precipitation method);

the pesticide is dissolved in an organic solvent which is not miscible with water, the solution is mixed turbulently with an aqueous solution of the saccharide, and the organic solvent is optionally removed (emulsifying method, optionally combined with evaporation);

a melt comprising molten pesticide is mixed into an aqueous solution comprising the saccharide and cooled (melt emulsification); or the pesticide is milled in the presence of the saccharide (milling method).

Specifically suitable is a method in which the saccharide is brought into aqueous solution, the pesticide dissolved in a water-miscible organic solvent, and the solutions of saccharide and pesticide are mixed turbulently (precipitation method).

In most cases, the solution of a pesticide in a water-miscible organic solvent comprises a water-miscible organic solvent. Water-miscible means in this context that the organic solvents are miscible with water at 20° C. without phase separation to at least 10% by weight, preferably to 15% by weight, especially preferably to 20% by weight. Optionally, the solution may comprise further formulation adjuvants, for example dispersants. If required, the solution may be prepared at elevated temperature. Suitable solvents are $C_1$-$C_6$-alkyl alcohols such as methanol, ethanol, propanol, isopropanol, 1-butanol, 2-butanol, tert-butanol, esters, ketones such as acetone, methyl ethyl ketone, methyl isopropyl ketone, methyl isobutyl ketone, acetals, ethers, cyclic ethers such as tetrahydrofuran, aliphatic carboxylic acids such as formic acid, acetic acid, propionic acid, N-substituted or N,N-disubstituted carbonamides such as acetamide, carboxylic esters such as, for example, ethyl acetate, and lactones such as, for example, butyrolactone, dimethylformamide (DMF) and dimethylpropionamide, aliphatic and aromatic hydrochlorocarbons such as methylene chloride, chloroform, 1,2-dichloroethane or chlorobenzene, N-lactams, glycols such as ethylene glycol or propylene glycol, and mixtures of abovementioned solvents. Preferred solvents are glycols, methanol, ethanol, isopropanol, dimethylformamide, N-methylpyrrolidone, methylene chloride, chloroform, 1,2-dichloroethane, chlorobenzene, acetone, methyl ethyl ketone, methyl isopropyl ketone, methyl isobutyl ketone, tetrahydrofuran, and mixtures of abovementioned solvents. Especially preferred solvents are propylene glycol, methanol, ethanol, isopropanol, dimethylformamide and tetrahydrofuran, in particular propylene glycol.

The aqueous solution of the saccharide usually comprises at least one monosaccharide, at least one disaccharide or a mixture of mono- and disaccharides. The total content of mono- and disaccharide amounts to at least 15% by weight, preferably to at least 20% by weight, especially preferably to at least 25% by weight, based on the aqueous solution. The solution may optionally comprise further formulation adjuvants, for example dispersants.

For carrying out the turbulent mixing, generally known methods are known to the skilled worker. The process step can be carried out batchwise, for example in a stirred vessel, or continuously. Continuously operating machines and apparatuses for emulsification are, for example, colloid mills, toothed-ring dispersers and other structural shapes of dynamic mixers, furthermore high-pressure homogenizers, pumps with downstream nozzles, valves, membranes or other narrow slit geometries, static mixers, inline mixers operating on the rotor/stator principle (Ultra-Turrax, Inline Dissolver), micro-mixing systems and ultrasonic emulsifier systems. It is preferred to employ toothed-ring dispersers or high-pressure homogenizers. In a further preferred embodiment, the turbulent mixing may take place in a mixing chamber. The temperature of the solutions employed can be from 20 to 200° C., preferably 50 to 150° C.

The dispersion prepared by the method according to the invention can be diluted or used further as such. It is furthermore possible to concentrate or to dry the aqueous dispersion. In a preferred embodiment, the aqueous dispersion is dried. Drying can be performed for example by spray-drying. The water content of the resulting solid composition frequently amounts to not more than 10% by weight, preferably to not more than 3% by weight, in particular 0.5% by weight.

Usually, a pesticide as described above is employed in the method according to the invention. It is preferred to employ a pesticide which is insoluble in water. The saccharides employed in the method in most cases are the above-described saccharides, in particular sucrose.

Further formulation adjuvants may optionally be added before, during or after the method. Formulation adjuvants are, for example, solvents, surfactants, inorganic emulsifiers (known as Pickering emulsifiers), antifoams, thickeners, antifreeze agents, and bactericides. Formulations intended for seed treatment may additionally also comprise adhesives and optionally pigments.

Suitable solvents are water, organic solvents such as mineral oil fractions of medium to high boiling point such as kerosine and diesel oil, furthermore, coal tar oils and oils of vegetable or animal origin, aliphatic, cyclic and aromatic hydrocarbons, for example paraffins, tetrahydronaphthalene, alkylated naphthalenes and their derivatives, alkylated benzenes and their derivatives, alcohols such as methanol, ethanol, propanol, butanol and cyclohexanol, glycols, ketones such as cyclohexanone, gamma-butyrolactone, dimethyl fatty acid amides, fatty acids and fatty acid esters, and strongly polar solvent, for example amines such as N-methylpyrrolidone. In principle, it is also possible to use solvent mixtures, and mixtures of the abovementioned solvents and water. It is preferred to add the abovementioned solvents only after the method, when a dispersion of the pesticide has formed.

In most cases, the aqueous dispersion according to the invention comprises no more than 30% by weight, preferably no more than 20% by weight, in particular no more than 10% by weight, of organic solvent.

In general, anionic, cationic and/or nonionic surfactants are added. Conventionally used anionic surfactants are, for example, ethoxylated mono-, di- and tri-alkylphenols (degree of ethoxylation of from 3 to 50, alkyl radical: $C_4$ to $C_{12}$) and ethoxylated fatty alcohols (degree of ethoxylation of from 3 to 80; alkyl radical: $C_8$ to $C_{36}$). Examples are the Lutensol® A brands ($C_{12}$ to $C_{14}$-fatty alcohol ethoxylates, degree of ethoxylation of from 3 to 8), Lutensol® AO brands ($C_{13}$ to $C_{15}$-oxoalcohol ethoxylates, degree of ethoxylation of from 3 to 30), Lutensol® AT brands ($C_{16}$ to $C_{18}$-fatty alcohol ethoxylates, degree of ethoxylation of from 11 to 80), Lutensol® ON brands ($C_{10}$-oxoalcohol ethoxylates, degree of ethoxylation of from 3 to 11) and the Lutensol® TO brands ($C_{13}$-oxoalcohol ethoxylates, degree of ethoxylation of from 3 to 20) from BASF SE. Others which are suitable are amphiphilic polymers, for example as described in EP 1 756 188 B1, paragraphs [0012] to [0068], or in DE 10 2006 001 529 A1, paragraphs [0025] to [0055], or based on the monomers acrylic acid, butyl methacrylate, methyl methacrylate, hydroxyethyl methacrylate and/or isobutyl methacrylate. Also suitable are amphiphilic block polymers, in particular based on ethylene oxide-propylene oxide. Examples are Pluronic® PE brands (EO-PO-EO tri-block polymers; EO: ethylene oxide, PO: propylene oxide). Others which are suitable are comb polymers, especially based on alkoxypolyoxyalkylene (meth)acrylates, such as comb polymers of methyl methacrylate, methacrylic acid and (methoxypolyethylene glycol) methacrylate (commercially available as Atlox® 4913 from Uniqema). Others which are conventionally used are polysaccharides and their derivatives, preferably polysaccharides based on inulin, for example Inutec® SP1 (inulin from chicory with grafted alkyl groups).

Examples of conventionally used anionic surfactants are alkali metal and ammonium salts of alkyl sulfates (alkyl radical: C8 to C12), for example sodium dodecyl sulfate, of sulfuric acid semiesters of ethoxylated alkanols (degree of ethoxylation of from 4 to 30, alkyl radical: $C_{12}$ to $C_{18}$) and ethoxylated alkylphenols (degree of ethoxylation of from 3 to 50, alkyl radical: $C_4$ to $C_{12}$), of alkylsulfonic acids (alkyl radical: $C_{12}$ to $C_{18}$) and of alkylaryl sulfonic acids (alkyl radical: $C_9$ to $C_{18}$). Furthermore, compounds of the general formula (I)

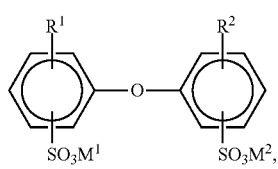

(I)

in which $R^1$ and $R^2$ are H atoms or $C_4$- to $C_{24}$-alkyl and are not simultaneously H atoms, and $M^1$ and $M^2$ can be alkali metal ions and/or ammonium ions, have further proved themselves as anionic surfactants. In the general formula (I), $R^1$ and $R^2$ are preferably linear or branched alkyl radicals having 6 to 18 C atoms, in particular having 6, 12 and 16 C atoms, or hydrogen, where $R^1$ and $R^2$ are not both simultaneously H atoms. $M^1$ and $M^2$ are preferably sodium, potassium or ammonium, with sodium being especially preferred. Especially advantageous are compounds (I) in which $M^1$ and $M^2$ are sodium, $R^1$ is a branched alkyl radical having 12 C atoms, and $R^2$ is an H atom or $R^1$. Frequently, one will use technical mixtures which comprise an amount of from 50 to 90% by weight of the monoalkylated product, such as, for example, Dowfax® 2A1 (brand of Dow Chemical Company). Others which are suitable are salts of dialkylsulfosuccinates, such as sodium dioctylsulfosuccinate (commercially available as Lutensit® A-BO from BASF SE). Furthermore suitable are arylphenol alkoxylates or their sulfated or phosphated derivatives, especially ethoxylated di- and tri-stryrylphenols or their sulfated or phosphated derivatives, such as Soprophor from Rhodia (ammonium salt of the ethoxylated tristyrylphenol sulfate with approximately 16 ethylene oxide groups per molecule). Likewise suitable are partially neutralized alkali metal salts of (meth)acrylic acid/maleic acid copolymers, for example the Sokalan® brands of BASF, in particular Sokalan CP45 (acrylic acid/maleic acid copolymer, sodium salt, partially neutralized).

Suitable cationic surfactants are, as a rule, cationic salts which have one $C_6$- to $C_{18}$-alkyl, -alkylaryl or heterocyclic radical, for example primary, secondary, tertiary or quaternary ammonium salts, alkanol ammonium salts, pyridinium salts, imidazolinium salts, oxazolinium salts, morpholinium salts, thiazolinium salts, and salts of amine oxides, quinolinium salts, isoquinolinium salts, tropylium salts, sulfonium salts and phosphonium salts. Examples which may be mentioned are dodecylammonium acetate or the corresponding sulfate, the sulfates or acetates of the various 2-(N,N,N-trimethylammonium)ethyl paraffinic esters, N-cetylpyridinium sulfate, N-laurylpyridinium sulfate and N-cetyl-N,N,N-trimethylammonium sulfate N-dodecyl-N,N,N-trimethylammonium sulfate, N-octyl-N,N,N-trimethylammonium sulfate, N,N-distearyl-N,N-dimethylammonium sulfate and the Gemini surfactant N, N'-(lauryldimethyl)-ethylenediamine disulfate, ethoxylated tallow fatty alkyl N-methylammonium sulfate and ethoxylated oleylamine (for example Uniperol® AC from BASF SE, approximately 12 ethylene oxide units). What is essential is that the nucleophilicity of the anionic counter groups is as low as possible, such as, for example, perchlorate, sulfate, phosphate, nitrate and carboxylates such as acetate, trifluoroacetate, trichloroacetate, propionate, oxalate, citrate, benzoate, and conjugated anions of organosulfonic acids such as, for example, methylsulfonate, trifluoromethylsulfonate and para-toluenesulfonate, furthermore tetrafluoroborate, tetraphenylborate, tetrakis(pentafluorophenyl)borate, tetrakis[bis(3,5-trifluoromethyl)phenyl]borate, hexafluorophosphate, hexafluoroarsenate or hexafluoroantimonate.

The concentration of surfactant added or its mixture can vary within wide ranges. Usually, concentrations of from 0.1 to 30% by weight, based on the aqueous dispersion, are used.

Examples of inorganic emulsifiers are metal salts, such as salts, oxides and hydroxides of calcium, magnesium, iron, zinc, nickel, titanium, aluminum, silicon, barium or manganese. The following should be mentioned: magnesium hydroxide, magnesium carbonate, magnesium oxide, calcium oxalate, calcium carbonate, barium carbonate, barium sulfate, titanium dioxide, alumina, aluminum hydroxide and zinc sulfide. Silicates, bentonite, hydroxyapatite and hydrotalcites may also be mentioned.

Examples of thickeners (compounds which impart a pseudoplastic rheology to the formulation, i.e. high viscosity at rest and low viscosity in the moved state) are, for example, polysaccharides such as xanthan gum, or organic sheet minerals.

Suitable antifoam agents are, for example, silicone emulsions, long-chain alcohols, fatty acids, organofluorine compounds and their mixtures.

Bactericides may be added to stabilize the aqueous formulation. Bactericides which may be present in the formulations according to the invention and which are suitable are all those bactericides conventionally used for the formulation of agrochemical active substances, such as, for example, dichlorophen and benzyl alcohol hemiformal.

Examples of suitable antifreeze agents are polyhydric alcohols such as ethylene glycol, propylene glycol or glycerol, preferably glycerol. From 0 to 30% by weight, preferably from 10 to 20% by weight, based on the aqueous solution, are generally added.

Adhesives which may be present in seed-dressing formulations and which are suitable are all binders which can conventionally be employed in seed-dressing products. The following may preferably be mentioned: polyvinylpyrrolidone, polyvinyl acetate, polyvinyl alcohol and tylose.

Moreover, colorants may also optionally be added to the formulations according to the invention. In this context, colorants which are suitable are all those conventionally used for such purposes, for example C.I. Pigment Red 48:2. In this context, both pigments, which are sparingly soluble in water, and dyes, which are soluble in water, can be used.

In general, it is not necessary to add crystallization inhibitors. It is preferred to add no more than 5% by weight, especially preferably no more than 1% by weight and specifically no crystallization inhibitors.

The present invention furthermore relates to a solid composition obtained by drying the dispersion according to the invention. The drying can be effected for example by spray-drying. Frequently, the water content of the solid composition is no more than 10% by weight, preferably no more than 3% by weight, in particular 0.5% by weight.

The invention furthermore relates to the use of a saccharide which is a monosaccharide, a disaccharide or a mixture of mono- and disaccharide for slowing down the particle growth of pesticide particles with a particle size of up to 10 μm in aqueous dispersion. Suppressing the particle growth means that, after storage of the dispersion for 24 h at 20° C., the particle size has increased less than in a comparative solution with less than 15% by weight of saccharide, preferably without saccharide.

The dispersion according to the invention, or the solid composition according to the invention can be used for controlling phytopathogenic fungi and/or undesired vegetation and/or undesired attack by insects or mites and/or for regulating the growth of plants, by allowing the dispersion or the solid composition to act on the respective pests, their environment and/or the plants to be protected from the respective pest, on the soil and/or on undesired plants and/or on the useful plants and/or their environment.

The dispersion according to the invention, or the solid composition according to the invention can be used for controlling undesired attack by insects or mites on plants and/or for controlling phytopathogenic fungi and/or for controlling undesired vegetation by treating seed of useful plants with the dispersion or the solid composition.

The invention furthermore relates to seed, treated, or preferably dressed, with the dispersion according to the invention or the solid composition according to the invention. In a preferred embodiment, the seed comprises the dispersion according to the invention or the solid composition according to the invention. Conventional seed-dressing methods can be employed for the treatment of seed. The seed treated in this way usually comprises the dispersion or solid composition.

The advantage of the present invention is that the aqueous dispersion of pesticide particles with a particle size of below 10 μm shows slowed-down particle growth, in particular by Ostwald ripening. A further advantage is that the particles settle more slowly and crystallize more slowly, or not at all. It is also advantageous that this stabilization of the dispersion was achieved with the aid of an environmentally-friendly agent, which is a saccharide. The method according to the invention has the advantage that it can be carried out with existing installations. Moreover, the saccharide employed allows easy and risk-free handling and is readily available without complicated synthesis. Furthermore, stable aqueous dispersions of pesticide particles can be obtained.

The examples which follow illustrate the invention without imposing any limitation.

EXAMPLES

Example 1

First, 16 g of pyraclostrobin were suspended in 144 g of propylene glycol for one hour, using 3 mm glass beads and a shaker (Red Devil). The resulting, still coarsely-particulate dispersion was conveyed through a mixing nozzle to a dissolving cell at a flow rate of 1 kg/h. There, propylene glycol was conveyed in at a temperature of 200° C. and a pumping rate of 2 kg/h. In the dissolving cell, the two strains were mixed turbulently, and a pyraclostrobin solution was generated.

The pyraclostrobin solution thus obtained was conveyed to a second mixing nozzle and mixed turbulently with a sucrose solution of 500 g of sucrose and 1000 g of water (i.e. 33.3% by weight) at a pumping rate of 16 kg/h. Before the conveying, the sucrose solution was cooled to 5° C. in a cryostat. The formation of pyraclostrobin particles takes place upon mixing. The amorphous pyraclostrobin precipitate thus obtained was discharged. An aqueous dispersion of 0.42% by weight of amorphous pyraclostrobin, which dispersion comprised 29.0% by weight of sucrose, was obtained. The particle sizes were determined over 24 h by means of laser diffraction (Malvern Mastersizer S) and laser scattering (Brookhaven Instruments BI90) (Tables 1 and 2).

For comparison purposes, the mixture was firstly repeated without the addition of sucrose and analyzed. Secondly, the experiment was repeated for comparison purposes, no sucrose being employed, but 4 g of sodium dodecyl sulfate (SDS) being added to the mixture of pyraclostrobin and propylene glycol. The aqueous suspension thus obtained comprised 0.42% by weight of pyraclostrobin and 0.1% by weight of SDS.

The experiments demonstrated that the formulations with sucrose show slowed-down particle growth in comparison with the formulation without sucrose or with SDS.

TABLE 1

Analysis of the particle size of pyraclostrobin (proportion <1 μm in %) by laser diffraction

| Time [h] | Without sucrose[a] | With SDS[a] | With sucrose |
|---|---|---|---|
| 0 | 100 | 100 | 100 |
| 1 | 97.6 | 100 | 100 |
| 2 | 92.2 | 98.2 | 100 |
| 3 | 81 | 94.2 | 97.6 |

TABLE 1-continued

Analysis of the particle size of pyraclostrobin (proportion <1 μm in %) by laser diffraction

| Time [h] | Without sucrose[a] | With SDS[a] | With sucrose |
|---|---|---|---|
| 4 | 74.6 | 87 | 99.1 |
| 5 | 69.1 | 87 | 94.4 |
| 6 | 64.9 | 77 | 89.5 |
| 24 | 50 | 30 | 67.2 |

[a]not according to the invention

TABLE 2

Analysis of the particle size (D in nm) of pyraclostrobin by means of laser scattering

| Time [h] | Without sucrose[a] | With SDS[a] | With sucrose |
|---|---|---|---|
| 0 | 291 | 256 | 253 |
| 1 | 584 | 500 | 311 |
| 2 | 685 | 580 | 508 |
| 3 | 787 | 670 | 490 |
| 4 | 845 | 680 | 531 |
| 5 | 850 | 730 | 607 |
| 6 | 889 | 807 | 563 |
| 24 | 1132 | 943 | 784 |

[a]not according to the invention

Example 2

In a stirred vessel, pulverulent pyraclostrobin and pulverulent epoxyconazole were heated to temperatures of from 80 to 90° C., during which process they melted. The mixture was stirred until a transparent single-phase liquid is present. In a second vessel, the continuous phase, composed of water, emulsifier A, emulsifier B and, optionally, sucrose, was made up and likewise heated to from 80 to 90° C. The melt mixture was then added to the continuous phase and, with the aid of a stirrer of the Ultraturrax® T 25 type dispersed in for 2 minutes at speed 6 at 24 000 revolutions/minute. In a high-pressure homogenizer (high-pressure pump G 400, Maximator GmbH, D-99734 Nordhausen), the crude emulsion thus prepared was processed at a temperature of approximately 85° C. at a homogenization pressure of 2000 bar. This gave a fine emulsion which was cooled directly after homogenization in an ice-water bath to temperatures of 20° C. or below at a cooling rate of 3.0 K/min, with stirring. This gave a suspension of solid, amorphous pesticide particles.

The following were present in product A (reference without sucrose):
3% by weight of epoxyconazole; 8% by weight of pyraclostrobin; 56% by weight of water; 30% by weight of emulsifier A (aqueous dispersion of an amphiphilic copolymer of the monomers acrylic acid, butyl methacrylate, methyl methacrylate, hydroxyethyl methacrylate and isobutyl methacrylate with a solids content of 33% by weight and a polymer particle size of approximately 10 to 60 nanometers); and 3% by weight of emulsifier B (aqueous solution of polyacrylic acid sodium salt, solids content 45% by weight, mean molar mass 1200 g/mol, commercially available as Sokalan® PA15 from BASF SE).

Product B according to the invention (with sucrose) had the same composition as product A, but the water was replaced by a mixture of sucrose/water in the weight ratio 8/1.

Samples were stored up to eleven days at room temperature, and characteristic parameters of the particle size distribution were determined by means of laser light diffraction.

Table 3 shows the course of the cubic particle size over time.

TABLE 3

Analysis of the particle size (x50 in μm) of pesticide particles

| Time [h] | Product A without sucrose[a] | Product B with sucrose |
|---|---|---|
| 0 | 0.881 | — |
| 2 | 0.965 | — |
| 3 | — | 0.632 |
| 5 | 0.991 | — |
| 6 | — | 0.646 |
| 23 | 1.104 | — |
| 24 | — | 0.685 |
| 264 | — | 0.865 |

[a]not according to the invention

The invention claimed is:

1. An aqueous dispersion comprising solid pesticide particles with a particle size of below 2 μm and a saccharide which is dissolved in the aqueous phase, wherein the saccharide is a monosaccharide, a disaccharide or a mixture of mono- and disaccharide, and the total content of mono- and disaccharide amounts to at least 15% by weight based on the aqueous dispersion, wherein the pesticide is insoluble in water, wherein the pesticide particles are amorphous, and wherein the pesticide particles are free from a polymeric coating composition.

2. The dispersion of claim 1, wherein the dispersion has a viscosity of at least 100 mPas at 20° C.

3. The dispersion of claim 1, wherein the total content of monosaccharide and disaccharide amounts to at least 20% by weight based on the aqueous dispersion.

4. The dispersion of claim 1, wherein the saccharide is a disaccharide.

5. The dispersion of claim 1, wherein the saccharide is sucrose.

6. The dispersion of claim 1, wherein the dispersion comprises at least 5% by weight of water.

7. A method for controlling pest selected from the group consisting of phytopathogenic fungi undesired vegetation, insects, and mites and/or for regulating the growth of plants, comprising applying the dispersion of claim 1 to the pests, an environment of the pests, and/or the plants to be protected from the pests, on soil and/or on undesired plants and/or on the useful plants and/or their environment.

8. The method of claim 7, wherein the dispersion has a viscosity of at least 100 mPas at 20° C.

9. The method of claim 7, wherein the total content of monosaccharide and disaccharide amounts to at least 20% by weight based on the aqueous dispersion.

10. The method of claim 7, wherein the saccharide is a disaccharide.

11. The method of claim 7, wherein the saccharide is sucrose.

12. The method of claim 7, wherein the dispersion comprises at least 5% by weight of water.

13. A method for controlling undesired attack by insects or mites on plants and/or for controlling phytopathogenic fungi and/or for controlling undesired vegetation comprising treating seed of useful plants with the dispersion of claim 1.

14. The method of claim 13, wherein the dispersion has a viscosity of at least 100 mPas at 20° C.

15. The method of claim 13, wherein the total content of monosaccharide and disaccharide amounts to at least 20% by weight based on the aqueous dispersion.

16. The method of claim 13, wherein the saccharide is a disaccharide.

17. The method of claim 13, wherein the saccharide is sucrose.

18. The method of claim 13, wherein the dispersion comprises at least 5% by weight of water.

19. A seed treated with the dispersion of claim 1.

* * * * *